United States Patent [19]
Cole

[11] Patent Number: 5,704,344
[45] Date of Patent: Jan. 6, 1998

[54] DEVICE FOR RELIEVING ANXIETY IN RESPIRATORY PATIENTS

[76] Inventor: Jeanne M. Cole, P.O. Box 171, Virginia City, Nev. 89440

[21] Appl. No.: 709,376

[22] Filed: Sep. 6, 1996

[51] Int. Cl.⁶ ............................................. A61M 17/00
[52] U.S. Cl. ............................. 128/200.14; 128/200.16
[58] Field of Search ................... 128/202.13, 203.23, 128/203.26, 203.16, 203.17, 200.14, 200.13, 200.24, 201.26, 201.23, 202.16, 203.12, 203.27, 207.18, 911, 912

[56] References Cited

U.S. PATENT DOCUMENTS 5,312,281  5/1994  Takahashi et al. .................. 446/25

FOREIGN PATENT DOCUMENTS 2081105   2/1982  United Kingdom ........... 128/200.16
WO 96/26755  9/1996  WIPO .......................... 128/200.16

OTHER PUBLICATIONS

C.R. McGavin, A Modified aerosol Inhaler for Teaching Technique, The Lancet, p. 1227, Dec. 4, 1976.

*Primary Examiner*—Vincent Millin
*Assistant Examiner*—Robert N. Wieland
*Attorney, Agent, or Firm*—Bielen, Peterson & Lampe

[57]  ABSTRACT

A patient device for assisting in the treatment of patients who use breathing devices is disclosed. The patient device includes a body which may have any of an infinite variety of shapes and appearances as long as the body is intended to appeal to and relieve the anxiety in the patient. In the preferred embodiment, the body incorporates an integrally formed mouth piece and/or face mask and channels for conducting gas. The device may also utilize visible vapor to produce a vapor effect which enhances the appearance of the patient device, further appeals to the patient, and encourages the patient to breath from the breathing device.

6 Claims, 2 Drawing Sheets

U.S. Patent     Jan. 6, 1998     Sheet 1 of 2     5,704,344
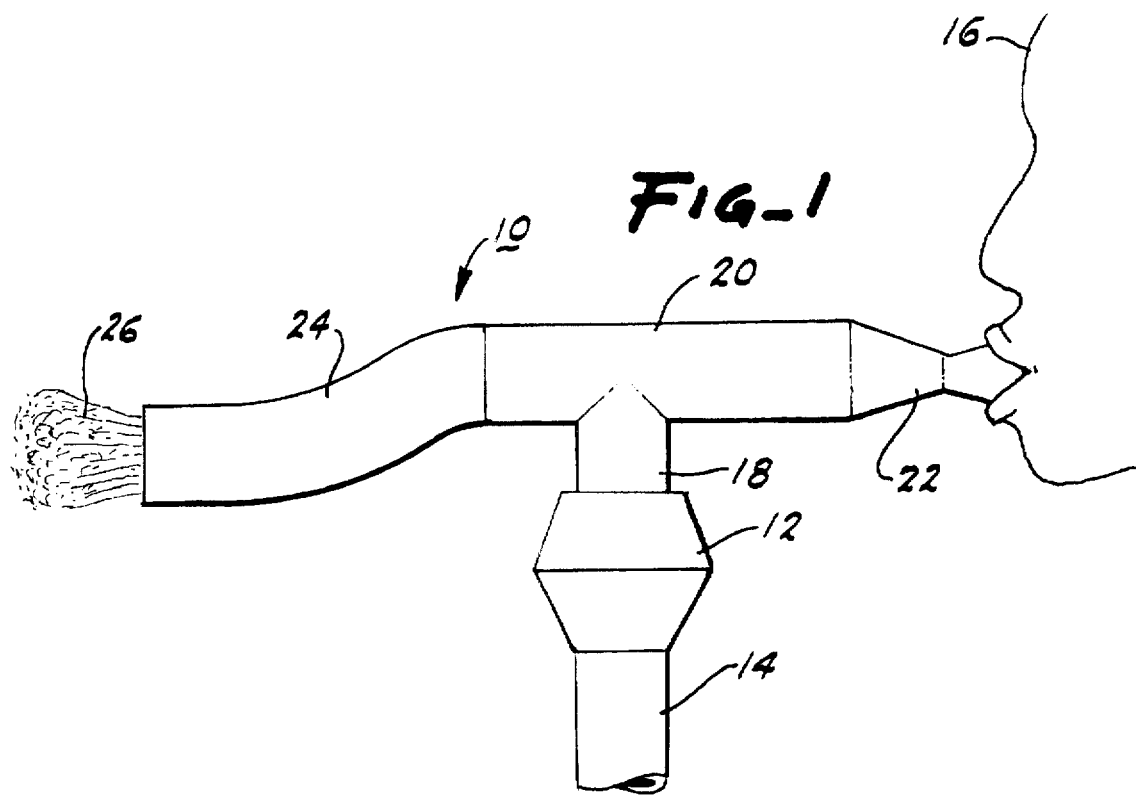
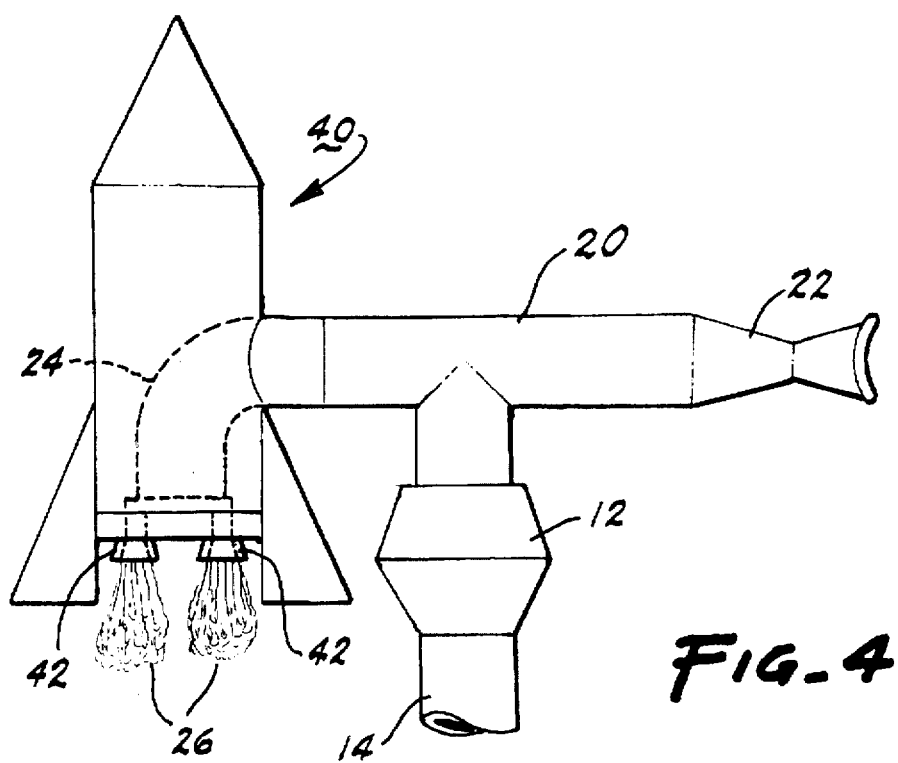

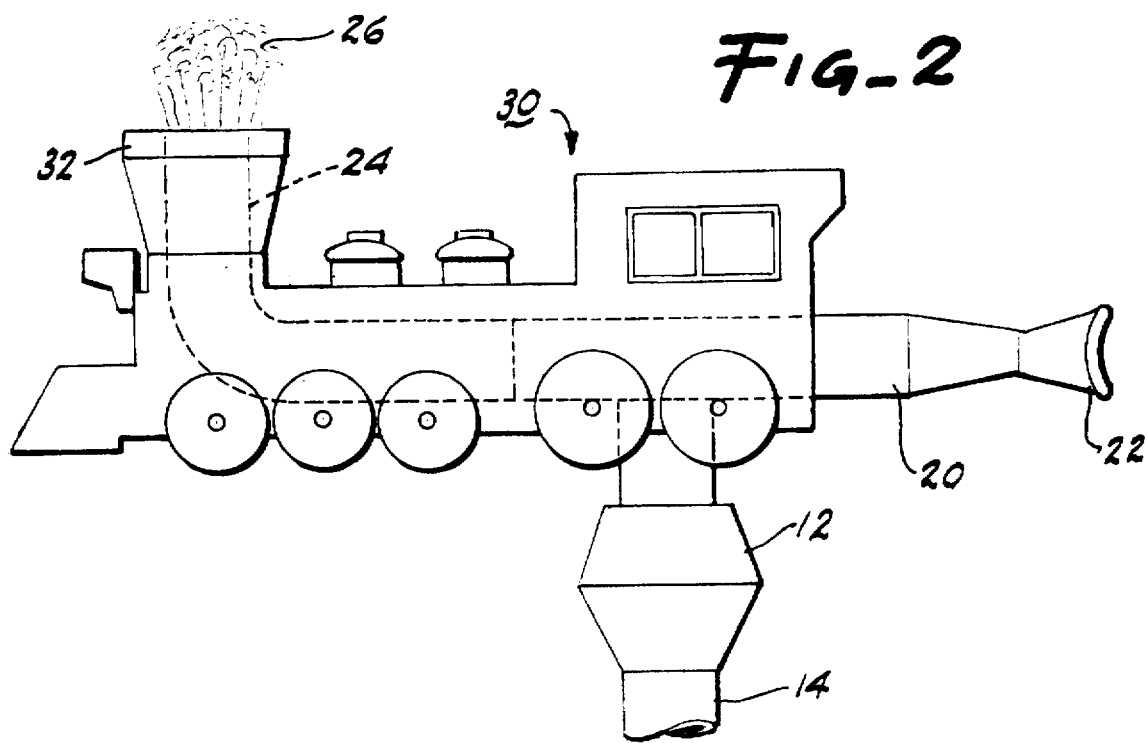
FIG_2
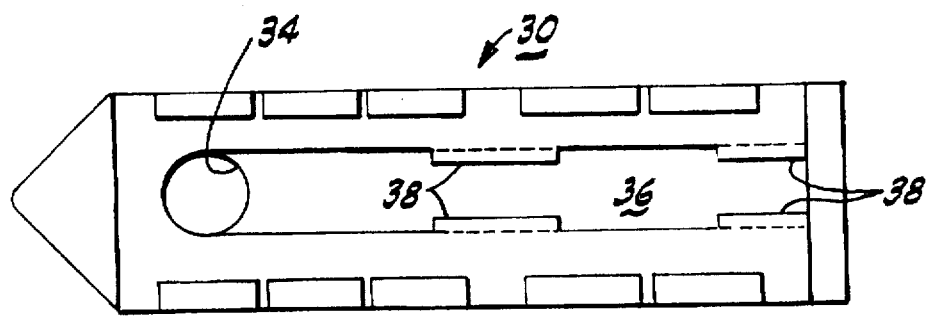
FIG_3

DEVICE FOR RELIEVING ANXIETY IN RESPIRATORY PATIENTS

BACKGROUND OF THE INVENTION

1. Field of Invention

The present invention relates to a device for relieving anxiety in respiratory patients who use breathing devices.

2. Description of Related Art

There are estimated to be four million children in the United States who suffer from diseases which effect their respiratory system. These diseases may include asthma, allergies, cystic fibrosis, pneumonia, and asthmatic bronchitis. Many of these children must use breathing devices to deliver aerosolized drugs to their lungs. These breathing devices vaporize liquid medication which is then drawn into the child's lungs as the child breaths.

However, breathing devices are often frightening to children. As is the case with most medical equipment, nebulizers and other breathing devices are designed for efficient operation and little or no thought is given to their appearance. Yet children are particularly susceptible to appearance and many parts of breathing devices, such as mouth pieces, masks, tubing, and pump assemblies, have a fightening appearance to children especially when a child is forced to use them The appearance of the breathing device combined with unusual noises, the unfamiliar setting of a hospital or clinic, and the urgency of medical treatment can result in a terrifying experience for children. The child's reaction to these circumstances can make it difficult to administer medication and the child's condition can be exacerbated.

SUMMARY OF INVENTION

1. Objects of the Invention

It is an object of the present invention to provide a patient device which relieves anxiety in patients who use breathing devices such as nebulizers.

It is another object of the invention to provide a patient device which may be used with large variety of existing breathing equipment without the need for modifications to the equipment.

It is another object of the invention to provide a patient device which does not interfere with the normal operation of the breathing equipment with which it is used.

It is another object of the invention to provide a patient device which may be easily and inexpensively manufactured.

It is another object of the invention to provide a patient device which utilizes visible exhaust vapor to create a vapor effect which further entertains and distracts the patient.

A further object of the invention is to provide a patient device which may be made in a variety of shapes including contemporary characters which are known to children.

2. Brief Description of the Invention

In accordance with the above objectives, the present invention comprises a patient device which appeals to patients. The device may be any shape and color so as to represent a large variety of objects. It may be shaped as a train engine, a truck, a jet plane, a rocket, an animal, or a contemporary character. The best shape and color for any particular patient depends upon many factors such as the patients gender, age, mentality, personality, and interests.

In the preferred embodiment, the patient device is attached to and covers breathing device tubing immediately in font of the patient when the patient is using the breathing device. In this way, the patient device is immediately in front of the patient and it provides an object upon which the patient can concentrate. The device also hides from view much of the tubing which would otherwise be visible to the patient.

In the preferred embodiment, the device covers the exhaust tube through which exhaust gas escapes. The exhaust gas also carries with it visible vapors which may be used to create a captivating effect when used with the device. For example, the device may be shaped as a train engine and the exhaust can be channeled to the exhaust stack of the engine. When the patient exhales, the patient can see the visible exhaust vapors issuing from the exhaust stack which is reminiscent of actual trains. The same effect can be used with other shapes, such as rockets, jet planes, trucks, whales, and dragons. This is called a vapor effect.

In the preferred embodiment the device is a single integral trait and is formed by injection molding. The device maybe made to cover tubing or the device may itself include integral channels for conducting respirator gases. The device may also be designed to accommodate many different kinds of breathing equipment.

BRIEF DESCRIPTION OF THE DRAWINGS

FIG. 1 is a side view of one common breathing device.

FIG. 2 is a side view of one embodiment of the present invention in use with a breathing device.

FIG. 3 is a bottom view of the embodiment of the present invention shown in FIG. 2.

FIG. 4 is a side view of another embodiment of the present invention in use with a breathing device.

REFERENCE NUMERALS 10 breathing device
12 nebulizer
14 tube
16 patient
18 lower portion
20 T-fitting
22 mouth piece
24 flexible tube
26 visible vapor
30 patient device
32 smoke stack
34 hole
36 slot
38 tabs
40 patient device
42 nozzle

DESCRIPTION OF THE PREFERRED EMBODIMENT

FIG. 1 depicts a commonly used breathing device 10 which may be used with the present invention. A nebulizer 12 is connected to an air or oxygen source which is supplied through robe 14. As air is forced into nebulizer 12, liquid medicine in nebulizer 12 is vaporized in a manner that is well known in the art so that it may be inhaled by a patient 16. The vaporized medication or medicinal vapor and air travel upwards though a lower portion 18 of a T-fitting 20. A mouth piece 22, engageable by the mouth of patient 16, is connected to T-fitting 20 so that patient 16 may inhale through the patient's mouth. Alternatively, a face mask (not shown) may also be used with nebulizer 12 so that the patient may inhale through both the patient's mouth and nose. Excess vapor and air and the patient's exhaled breath normally escape through a flexible tube 24. This exhaust normally includes visible vapor 26.

As seen in FIG. 2, the present invention comprises a patient device or decorative member 30 which may cover or incorporate much of the tubing of a respirator apparatus including T-fitting 20 and tube 24, which serves as an exit for gases. Device 30 may be of any shape and color. However, device 30 is intended to be appealing to the patient so that it will attract and hold the attention of the patient. Device 30 in FIG. 2 is shaped like a train engine with a smoke stack 32. In this embodiment it is possible to create a captivating "vapor effect" by channeling exhaust vapors through tube 24 to the top of smoke stack or decorative exhaust port 32. At this point the visible vapors 26 are released and it will appear to the patient that the train engine is producing exhaust. As the patient breaths from the breathing device puffs of visible vapors 26 are produced. The more the patient breaths from the respirator, the more the interesting vapor effect can be seen. In this way, the patient is encouraged to breath from the respirator and receives positive reinforcement.

Device 30 may be made so that T-fitting 20, mouth piece 22, and tube 24 can be inserted into device 30. In this embodiment, as seen in FIG. 3, device 30 may have a groove or slot 36 on the bottom surface of device 30 for receiving the various parts. A hole 34 is provided for directing tube 24 to the top of smoke stack 32.

Retaining means, such as tabs 38, may also be provided for holding the various components in device 30. In an alternative embodiment, T-fitting 20, mouth piece 22, and/or tube 24 are integrally formed in device 30. Nebulizer 12 with tube 14 need only be attached to device 30 to supply the vaporized medication. This embodiment has the advantage of reducing the total cost of the breathing device and making the breathing device quicker and easier to assemble. It is recognized that nebulizer 12 and tube 14 may also be integrally formed with device 30.

In the preferred embodiment, device 30 is injection molded which allows the device to be inexpensively produced. However, other methods of manufacturing may be used. In the embodiment in which T-fitting 20, mouth piece 22, and/or tube 24 are integrally formed, device 30 is preferably disposable so that the device may be discarded after one use in order to reduce the risk of spreading contagious diseases.

FIG. 4 represents an alternative configuration of the present invention. In this embodiment, a device 40 is shaped as a rocket and it is attached to either T-fitting 20 or tube 24. As the patient exhales, the exhaust is channeled downward through tube 24 in device 40 and exits through nozzles 42. This configuration makes visible vapors 26 appear as rocket exhaust. Device 42 may also be shaped so as to appear as the space shuttle or any other space vehicle.

Although the present invention is primarily intended for use with young patients, it is recognized that other patients, such as mentally disabled patients, may also benefit from the invention. In addition, derivatives of the present invention may also be used with adult patients. These derivations may include puzzles or games which would provide some mental stimulation to the patient.

Although the description above contains many specifications, these should not be construed as limiting the scope of the invention but as merely providing illustration of some of the presently preferred embodiment of this invention. In particular, devices 30 and 40 are intended as examples of the infinite varieties of shapes the invention may take. Thus, the scope of the invention should be determined by the appended claim and their legal equivalent rather than by the examples given.

What is claimed is:

1. A device for altering the external appearance of a nebulizer, useable by a patient, having an output of medicinal vapor and an output conduit to conduct the medicinal vapor comprising:

a. a tube connected to the output conduit of the nebulizer, said tube having a first patient mouth engageable end portion and a second gas exit end portion to carry visible exit gases from the mouth of the patient;

b. a decorative member at least partially surrounding said tube, said member including a decorative exhaust port;

c. means for connecting said tube second gas exit end portion to said decorative exhaust port to direct visible exit gases therethrough.

2. The device of claim 1 in which said decorative member includes a groove for at least partially accommodating said tube.

3. The device of claim 2 in which said tube includes a central portion forming a tee fitting with the output conduit of the nebulizer, said first patient mouth engageable end portion and said second gas exit end portion connected to said tube central portion for communication therewith.

4. The device of claim 1 in said decorative member and said tube are integrally formed.

5. The device of claim 1 in which said decorative exhaust port includes an angular conduit for altering the direction of exit gases from said tube.

6. The device of claim 1 in which said decorative exhaust port positions outwardly from said first patient mouth engageable end portion for viewing by the patient.

* * * * *